US00PP20608P2

(12) United States Plant Patent
Catt

(10) Patent No.: US PP20,608 P2
(45) Date of Patent: Dec. 22, 2009

(54) ***CARYOPTERIS* PLANT NAMED 'LISAURA'**

(50) Latin Name: *Caryopteris×incana*
Varietal Denomination: LISAURA

(76) Inventor: Peter Catt, Liss Forest Nursery Ltd Petersfield Road, Greatham, Liss Hants (GB) GU33 6HA ( * ) Notice: Subject to any disclaimer, the term of this patent is extended or adjusted under 35 U.S.C. 154(b) by 0 days.

(21) Appl. No.: 12/220,881

(22) Filed: Jul. 28, 2008

(51) Int. Cl.
*A01H 5/00* (2006.01)

(52) U.S. Cl. ..... Plt./226

(58) Field of Classification Search ..... Plt./226
See application file for complete search history.

(56) References Cited

OTHER PUBLICATIONS

UPOV Plant Variety Database 2008/06 p. 1.*

* cited by examiner

*Primary Examiner*—Annette H Para

(57) ABSTRACT

A new and distinct cultivar of *Caryopteris* named 'LISAURA' that is characterized by upright habit, aromatic golden color foliage, and scented amethyst-blue flowers. In combination these traits set 'LISAURA' apart from all other existing varieties of *Caryopteris* known to the inventor.

3 Drawing Sheets

Genus: *Caryopteris*.
Species: ×*incana*.
Denomination: 'LISAURA'.

BACKGROUND OF THE INVENTION

The present invention relates to a new variety of *Caryopteris*, commonly known as bluebeard, which is grown as an ornamental shrub grown for use in the garden and landscape, and as a container plant. The new invention is known botanically as *Caryopteris×incana* and will be referred to hereinafter by the cultivar name 'LISAURA'.

The inventor has been interested in the genus *Caryopteris* and its breeding potential since 1998. Commencing in 1998, the inventor acquired plants of existing cultivars of the species *Caryopteris×clandonensis* and also raised plants as seedlings from these cultivars. The inventor's variety *Caryopteris×clandonensis* 'First Choice' (U.S. Plant Pat. No. 11,958) arose from this breeding programme.

The inventor has been particularly interested in raising gold-leafed forms of *Caryopteris*. There are very few gold-leafed varieties in commerce and the inventor feels that the characteristic blue flowers of *Caryopteris* present very well against golden foliage. However, the inventor is concerned that the golden foliage must not scorch or bleach in full sun.

In spring 1999, the inventor raised several seedlings from seed harvested during 1998 from the gold-foliaged cultivar *Caryopteris×clandonensis* 'Worcester Gold' (unpatented). These seedlings were observed for foliage color through the summer of 1999. One seedling was selected as having the best combination of gold leaf color and plant habit and vigor. The inventor grew and over-wintered this seedling and collected seed from it during summer 2000.

In 2000, in order to bring more variation into the breeding programme, the inventor decided to introduce the species *Caryopteris incana* which carries larger, broader leaves relative to *Caryopteris×clandonensis* and which bears its flowers all around the stem. In the fall of 2000, the inventor sowed a single row of seeds of *Caryopteris incana* in between a double row of the seeds which the inventor had collected from the gold-foliaged seedling of *Caryopteris×clandonensis*.

During 2001, after open pollination had taken place, the inventor collected seed from plants in the center row, namely from plants raised as *Caryopteris incana*. These seeds were sown immediately and the inventor observed that although the foliage size and shape was typical of *Caryopteris incana*, only two seedlings bore golden foliage. These two seedlings were transplanted to a garden border for over-wintering and were allowed to grow naturally for the following two years. The inventor selected one, 'LISAURA' in 2004.

'LISAURA' exhibits upright habit, aromatic, golden colored foliage, and scented amethyst-blue flowers that bloom in late summer. 'LISAURA' grows 46 cm. in height and 46 cm. in width during the first year, reaching 90 cm. in height and 90 cm. in width at maturity. Cultural needs include full sun, well-draining moderately fertile soil, and moderate water.

The closest comparison plant known to the inventor is the female parent, in as much as both plants exhibit similarly large and broad leaves. However, the gold-foliaged 'LISAURA' is readily distinguishable from the green-leafed female parent.

'LISAURA' may also be compared with the unknown male parent, a gold-foliaged seedling of *Caryopteris×clandonensis*. Although golden colored foliage is common to both, the leaves of 'LISAURA' are larger and broader and the flowers of 'LISAURA' completely circle the stem rather than being borne on one side of the stem.

The first asexual reproduction of 'LISAURA' was accomplished in 2004 at the inventor's nursery in Hampshire, United Kingdom. Asexual propagation was conducted using the method of softwood cuttings under mist. Since that time under careful observation 'LISAURA' has been determined fixed, stable and to reproduce true to type in subsequent generations of asexual propagation.

The inventor filed an application for European Community Plant Breeders' Rights for 'LISAURA' on Feb. 19, 2007, Serial No. 2007/0448. The inventor made the first public sale or distribution of 'LISAURA' on Aug. 12, 2007.

SUMMARY OF THE INVENTION

The following traits have been repeatedly observed and represent the distinguishing characteristics of the new *Caryopteris* cultivar named 'LISAURA'. These traits in combination distinguish 'LISAURA' from all other existing varieties of *Caryopteris* known to the inventor. 'LISAURA' has not been tested under all possible conditions. Phenotypic differences may be observed with variations in environmental, climatic, and cultural conditions without however any variance in genotype.

1. 'LISAURA' exhibits upright habit.
2. 'LISAURA' exhibits aromatic, golden colored foliage.
3. 'LISAURA' exhibits scented amethyst-blue flowers.
4. 'LISAURA' reaches 90 cm. in height and 90 cm. in spread at maturity.
5. 'LISAURA' blooms in late summer.
6. 'LISAURA' is hardy to USDA Zones 6.

BRIEF DESCRIPTION OF THE DRAWINGS

The accompanying color drawings illustrate the overall appearance of 'LISAURA' showing color as true as is reasonably possible to obtain in color reproductions of this type. Color in the drawings may differ from color values cited in the detailed botanical description, which accurately describe the actual color of the new variety 'LISAURA'.

The drawing labeled

The drawing labeled

Figure 1:
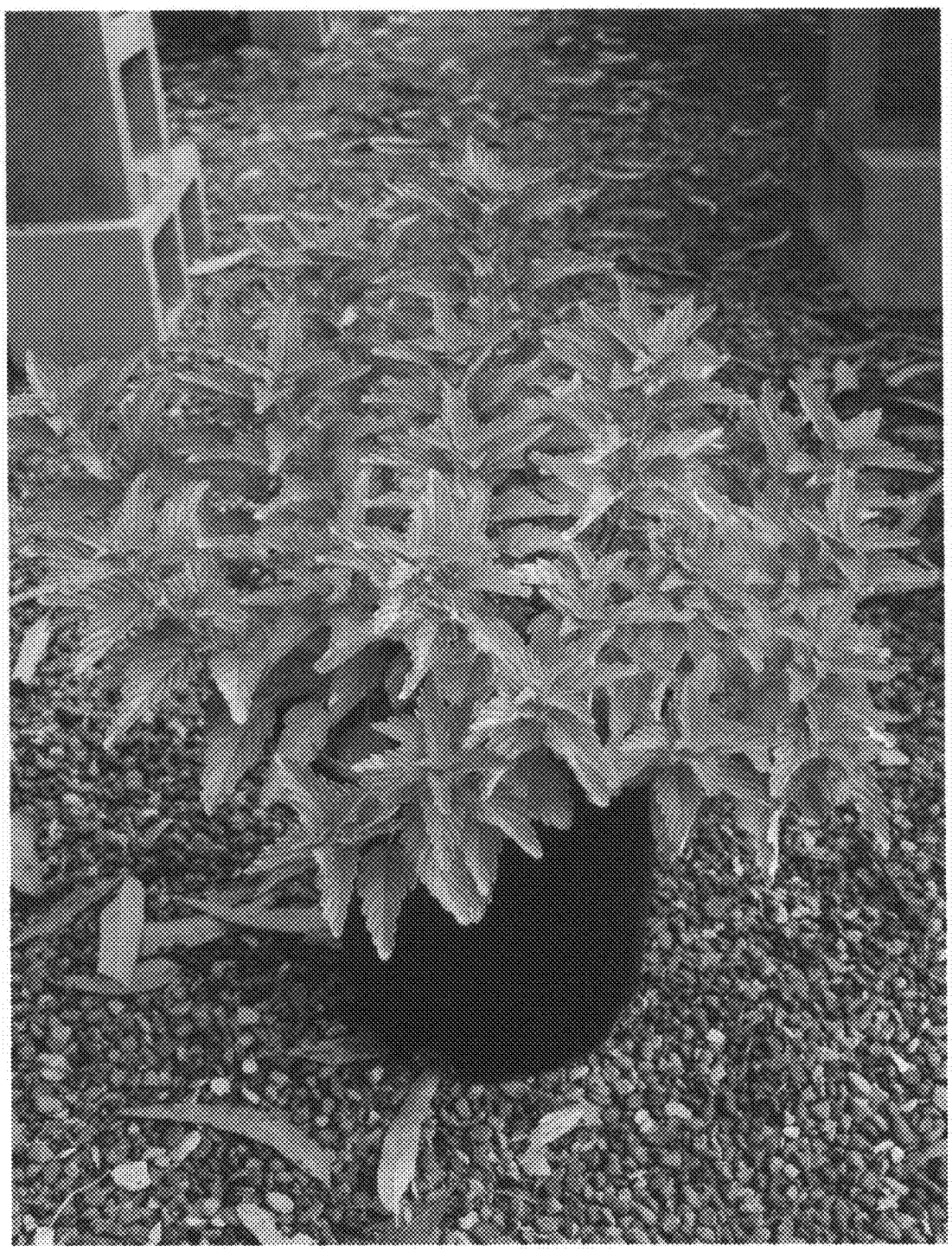
FIG. 1 depicts a nine months old plant which has been grown out of doors in a 1 liter container in Arroyo Grande, Calif.
Figure 2:
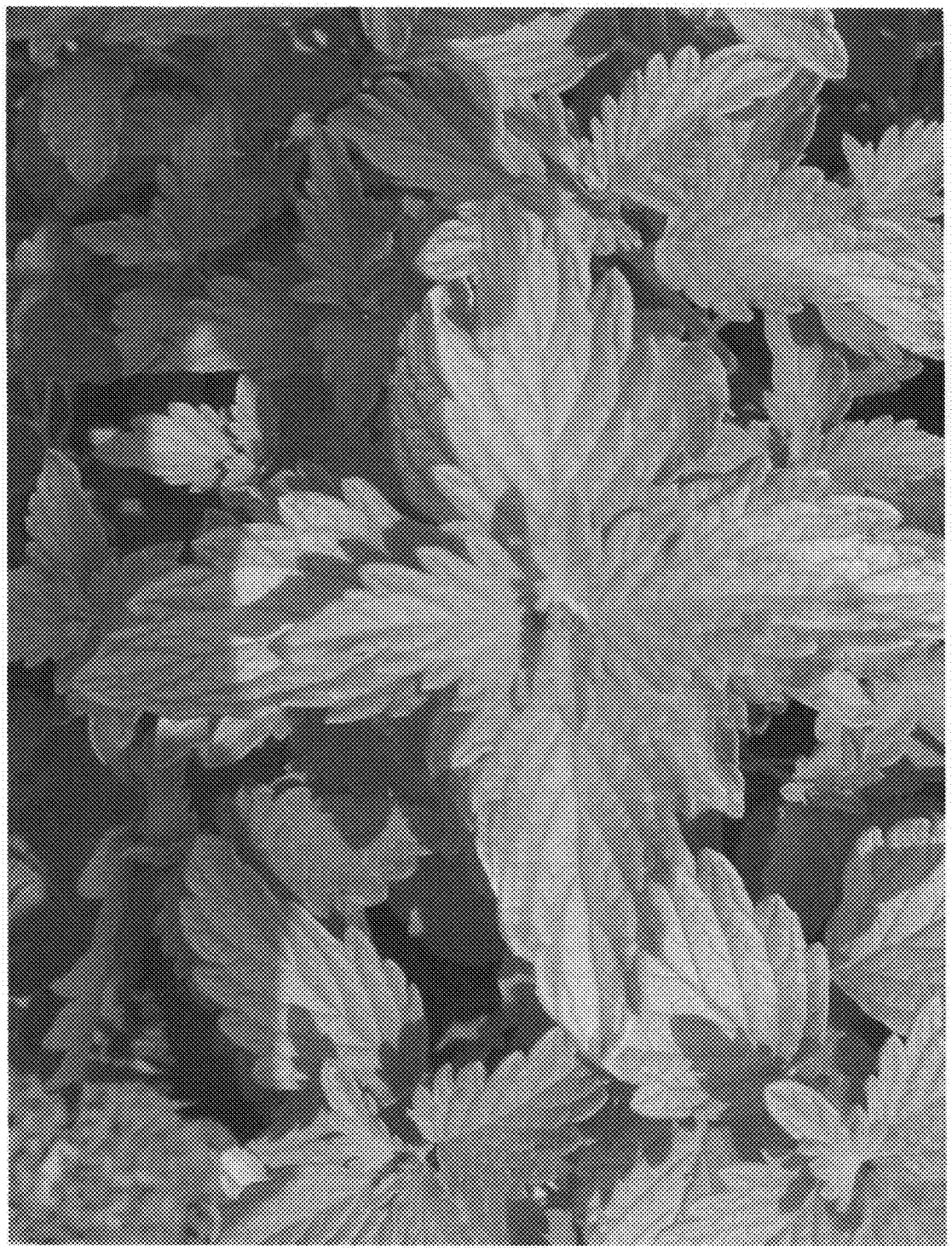
FIG. 2 presents a close up view of the foliage of the plant illustrated in FIG. 1.
Figure 3:
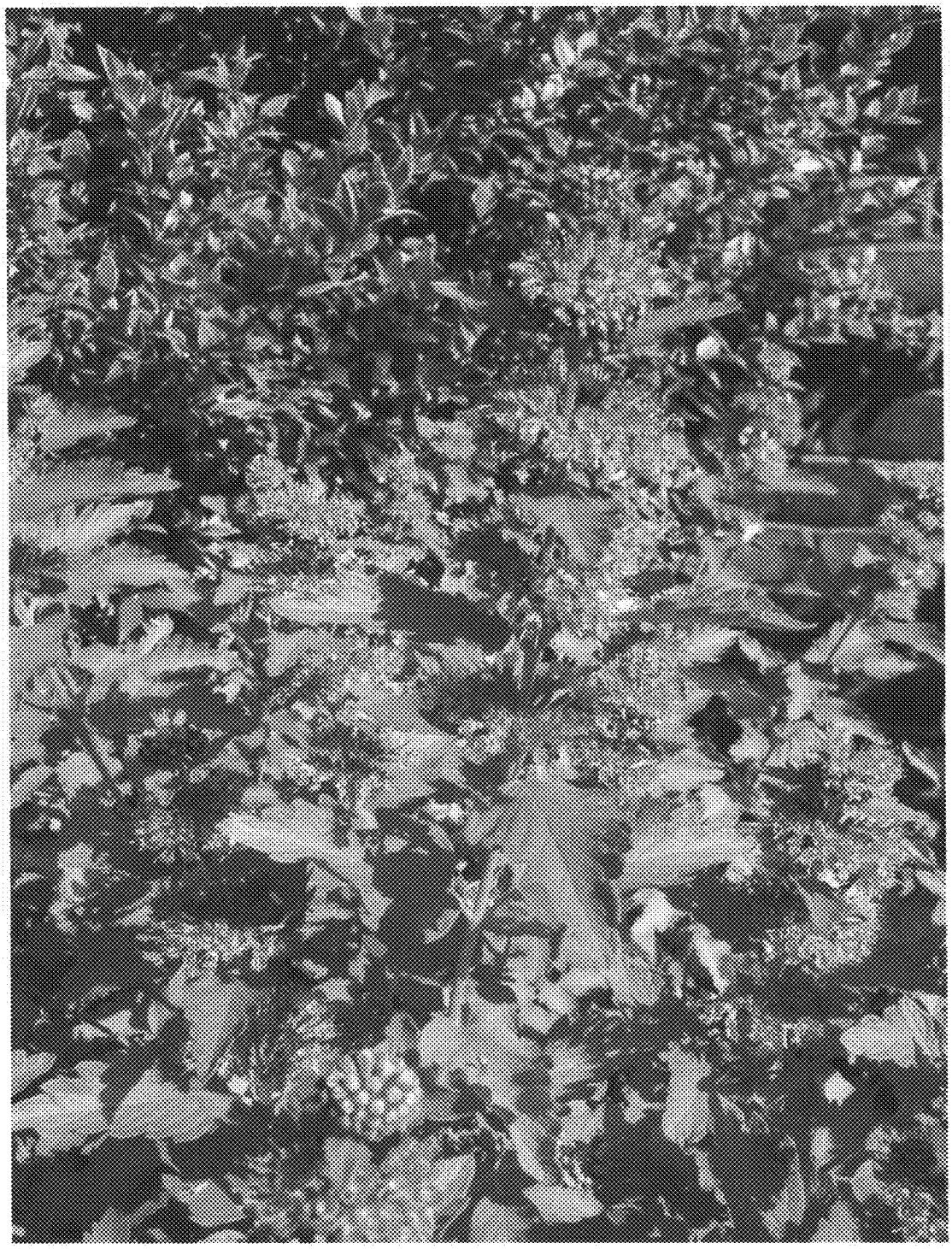

The drawing labeled as FIG. 3 illustrates the flowers and the buds of the plant illustrated in FIG. 1, at an age of approximately ten months.

All the drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Caryopteris* cultivar named 'LISAURA'. Observations, measurements, values and comparisons were collected from a plant which had been grown out of doors in Arroyo Grande, Calif., in a 1 liter container. The plant was observed from 9 months to 12 months of age.

Color determinations are made in accordance with The 2001 Royal Horticultural Society Colour Chart from London, England, except where general color terms of ordinary dictionary significance are used. The growing requirements of the new variety 'LISAURA' are similar to the species.

Botanical classification: *Caryopteris*×*incana* 'LISAURA'.

Family: Verbenaceae.

Genus: *Caryopteris.*

Species: ×*incana.*

Denomination: 'LISAURA'.

Common name: Bluebeard.

Habit: Upright.

Commercial category: Ornamental shrub.

Use: For mixed border and the landscape, and for planting in containers. Suggested commercial container size: 1-litre container.

Parentage: *Caryopteris*×*incana* 'LISAURA' is a seedling selection resulting from deliberate open cross-pollination of the following parents:

*Female parent.*—*Caryopteris incana* (unpatented).

*Male parent.*—*Caryopteris*×*clandonensis* 'Gold Seedling' (unpatented).

Propagation method: Softwood cuttings.

Rooting system: Fine.

Vigor (range): Low to moderate.

Crop time (range): 9–12 months to produce a 1-litre container from stem cuttings.

Temperature (range): The recommended air temperature is 20°–21° Centigrade.

Plant dimensions (first year): 46 cm. in height and 46 cm. in width.

Plant dimensions (at maturity): 90 cm. in height and 90 cm. in width.

Cultural requirements: Grow in well-draining reasonably fertile soil and full sun, with moderate water.

Pest susceptibility: Susceptible to aphids.

Disease susceptibility: None known to the inventor.

Hardiness: USDA Zones 6.

Special considerations: Cut back hard to woody frame in spring.

Stem:

*Trunk dimensions.*—2 cm. in height and 0.60 cm. in width.

*Trunk color.*—197A.

*Trunk surface.*—Scurfy.

*Shape.*—Subcylindrical.

*Surface.*—Pubescent.

*Color.*—146D and 182B.

*Stem length* (*average*).—18 cm.

*Stem diameter* (*average*).—0.25 cm.

*Internode* (*average*).—2.25 cm.

Foliage:

*Type.*—Deciduous.

*Leaf arrangement.*—Opposite.

*Leaf division.*—Simple.

*Leaf margin* (*range*).—Serrate to entire.

*Leaf surface* (*abaxial*).—Puberulent.

*Leaf surface* (*adaxial*).—Puberulent.

*Leaf shape.*—Ovate.

*Leaf length* (*range*).—3 cm. to 5.50 cm.

*Leaf width* (*range*).—2.20–3 cm.

*Leaf color* (*abaxial surface*).—N144A and 153C.

*Leaf color* (*adaxial surface*).—N144C and 153D.

*Leaf apex* (*range*).—Acute to rounded.

*Leaf base.*—Rounded.

*Venation.*—Pinnate.

*Vein color* (*abaxial and adaxial surfaces*).—146D.

*Attachment* (*range*).—Clasping to petiolate.

*Petiole shape.*—Sulcate.

*Petiole surface.*—Pubescent.

*Petiole color.*—146D.

*Petiole dimensions.*—0.50 cm. in length and 1 mm. in width.

*Leaf fragrance.*—Aromatic.

Inflorescence:

*Type.*—Cyme.

*Inflorescence.*—dimensions (*average*).—1.50 cm. in length and 1.50 cm in width.

*Flower quantity* (*average*).—40 per inflorescence.

*Peduncle shape.*—Cylindrical.

*Peduncle surface.*—Puberulent.

*Peduncle color.*—138B.
*Peduncle dimensions* (*average*).—3.25 cm. in height and 4 mm. in width.
*Bud quantity* (*average*).—40 per inflorescence.
*Bud shape.*—Globose.
*Bud apex.*—Rounded.
*Bud color.*—91 D.
*Bud surface.*—Pubescent.
*Bud dimensions.*—3 mm. in length and 4 mm. in diameter.
*Corolla shape.*—Tubular.
*Corolla color.*—(*ventral and dorsal surface*).—96C.
*Corolla dimensions.*—1 cm. in depth and 5 mm. in width.
*Corolla surface* (*ventral and dorsal*).—Puberulent.
*Lobes.*—5 in number.
*Lobes fused or unfused.*—Fused.
*Lobe color* (*adaxial and abaxial surfaces*).—96C.
*Lobe margin.*—Fimbriate.
*Lobe surface* (*abaxial and adaxial*).—Puberulent.
*Lobe apex.*—Rounded.
*Calyx shape.*—Tubular.
*Calyx dimensions.*—3 mm. in length and 1 mm. in width.
*Sepals.*—5 in number.
*Sepals fused or unfused.*—Fused.
*Sepal color* (*abaxial and adaxial surfaces*).—N138B.
*Sepal margin.*—Entire.
*Sepal apex.*—Acute.
*Sepal surface* (*abaxial and adaxial*).—Puberulent.
*Inflorescence fragrance.*—Sweet scent.

Reproductive organs:
*Stamen quantity.*—4 in number.
*Stamen length.*—5 mm.
*Stamen color.*—N88D.
*Anther color.*—N187A.
*Anther length.*—<0.50 mm.
*Pollen amount.*—Low.
*Pollen color.*—N187A.
*Pistil quantity.*—1 in number.
*Pistil length.*—11 mm.
*Pistil color.*—N88D.
*Style.*—Bifid.
*Style color.*—N88D.
*Ovary position.*—Superior.
*Ovary shape.*—Globose.
*Ovary dimensions.*—1 mm. in height and 1 mm. in diameter.
*Ovary color.*—144A.

It is claimed:

1. A new and distinct cultivar of *Caryopteris* plant named 'LISAURA,' as described and illustrated herein.

* * * * *